United States Patent [19]
Li et al.

[11] Patent Number: 6,149,915
[45] Date of Patent: *Nov. 21, 2000

[54] TREATMENT OF DIABETIC NEPHROPATHY AND MICROALBUMINURIA

[75] Inventors: Hai-Ri Li, Mudanjiang, China; Hyun Chul Lee; Mankil Jung, both of Seoul, Rep. of Korea; Sudhir V. Shah, Little Rock, Ark.

[73] Assignee: Shiva Biomedical, LLC, Paramus, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/408,436

[22] Filed: Sep. 29, 1999

[51] Int. Cl.$^7$ ........................... A61K 35/78; A61K 31/36
[52] U.S. Cl. .......................... 424/195.1; 514/464
[58] Field of Search .......................... 424/195.1; 514/464

[56] References Cited

U.S. PATENT DOCUMENTS

| | | | |
|---|---|---|---|
| 5,358,962 | 10/1994 | Oura et al. | 514/469 |
| 5,547,945 | 8/1996 | Ye et al. | 514/54 |

FOREIGN PATENT DOCUMENTS

| | | |
|---|---|---|
| 01268682 | 10/1989 | Japan . |
| 07048265 | 2/1995 | Japan . |

OTHER PUBLICATIONS http://rich.chonnam.ac.kr/HRIC/research/resear13.htm, Aug. 9, 1999.

Yokozawa, T., et al., "Isolation of a renal fumction–facilitating constituent from the Oriental drug, Salviae Miltiorrhizae Radix", *Japanese Journal of Nephrology,* 31(10):91–98 (1989).

Yokozawa, T. et al., "Effects of a Dan Shen component, magnesium lithospermate B, in nephrectomized rats", *Japanese Journal of Nephrology,*37:105–111 (1995).

Baohua, S., et al., "Effects of Hypoxic Endothelial Cell Conditioned Medium on Proliferation and Collagen Synthesis of Smooth Muscle Cells and Inhibitory Effects of Radix Salviae Miltiorrhizae", *Chinese Medical Journal,* 108(11):855–858 (1995).

Yokozawa, T. et al., "Effects of magnesium lithospermate B on the renal and urinary kallikrein activities in rats with adenine–induced renal failure", *Japanese Journal of Nephrology,*35 (4):337–341 (27–31) (1993).

Yokozawa, T., et al., "Effects of (dihydro) caffeic acid tetramer isolated from Salviae Miltiorrhizae Radix on renal function", *Journal of Medical and Pharmaceutical Society for WAKAN–YAKU,* 5:163–166 (1988).

Yokozawa, T. et al., "A Protective Action of Magnesium Lithospermate B on Renal Function after Ischemia–Reperfusion of Rats and Cultured Proximal Tubular Cells", *Natural Medicines,* 51(4):287–292 (1997).

Yokozawa, T. et al., "Renal Responses to Magnesium Lithospermate B in Rats with Adenine–induced Renal Failure", *Phytotherapy Research,* 7:235–239 (1993).

Yokozawa, T. et al., "Effects of Dan Shen Preparations on Blood and Urine Components in Rats with Renal Failure", *Phytotherapy Research,* 7:231–234 (1993).

Yokozawa, T., et al. "Augmentation of Renal Response by Magnesium Lithospermate B", *Nephron,* 57:78–83 (1991).

Chung, H.Y., et al., "Renal Effect of Aqueous Extract from Salviae miltiorrhizae Radix in Normal Rats", *Chem Pharm Bull,* 35(6):2465–2469 (1987).

Yokozawa, T. et al., "Confirmation that Magnesiun Lithospermate B Ameliorates Paraquat–Induced Injury in Cultured Renal Epithelial Cells", *Nephron,* 79:373–374 (1998).

Yokozawa, T. et al., "Effect of Magnesium Lithospermate B in Rats with Sodium–Induced Hypertension and Renal Failure", *Nephron,*60:460–465 (1992).

Yokozawa, T. et al., "Contribution of Prostaglandins to the Renal Responses to Magnesium Lithospermate B Isolated from Salviae Miltiorrhizae Radix", *Chem Pharm Bull,* 37(6):1568–1571 (1989).

Mattock, M.B., et al., "Prospective Study of Microalbuminuria as Predictor of Mortality in NIDDM", *Diabetes,* 41:736–741 (1992).

Yokozawa, T., et al., "Renal Responses to Magnesium Lithospermate B", *J. Pharm. Pharmacol.,* 42:712–715 (1990).

Yokozawa, T., et al., "Magnesium Lithosprmate B Suppresses the Increase of Active Oxygen in Rats after Subtotal Nephrectomy", *Nephron,* 75:88–93 (1997).

Guoji, Y., et al., "Effects of Polysaccharides Purified from *Salviae miltiorrhizaeradix*on Experimental Nephrosis Rats", *Phytotheraphy Research,* 8:337–341 (1994).

Pegoraro, A.A., "Microalbuminburia: A Clinical Update", *Kidney:A Current Survey of World Literature,*8:1–5 (1999).

Abbott, K.C. et al., "Microalbuminuria in Non–Insulin–Dependent Diabetes Mellitus", *Arch Intern Med,*154:146–153 (1994).

Yokowaza, T., et al., "Isolation of the Active Component Having the Uremia–Preventive Effect from Salviae Miltiorrhizae Radix Extract", *Chem Pharm Bull,*36(1):316–320 (1988).

Neil, A., et al., "A Prospective Population–Based Study of Microalbuminuria as a Predictor of Mortality in NIDDM", *Diabetes Care,* 16(17):996–1003 (1993).

Yokozawa, T., et al., "Magnesium lithospermat B ameliorates cephaloridine–induced renal injury", *Exp Toxic Pathol* 49:337–341 (1997).

(List continued on next page.)

*Primary Examiner*—Raymond Henley, III
*Attorney, Agent, or Firm*—Hamilton, Brook, Smith & Reynolds, P.C.

[57] ABSTRACT

Diabetic nephropathy and microalbuminuria are treated with the herb Salviae Miltiorrhizae Radix. In one embodiment, the method includes boiling the herb to form an aqueous extract. The aqueous extract is administered to the diabetic individual to treat diabetic nephropathy or to an individual exhibiting microalbuminuria. Alternatively the method can include administering a salt of lithospermic acid extracted from the herb. The method can include determining the level of protein in urine before, during and/or after administering the aqueous extract or a salt of lithospermic acid.

52 Claims, 4 Drawing Sheets

OTHER PUBLICATIONS

Yokozawa, T., et al., "Magnesium Lithospermat B ameliorates cisplatin–induced injury in cultured renal epithelial cells", Exp Toxic Pathol, 49:343–346 (1997).

Yokozawa, T., et al., "Effects on Blood Pressure of Caffeic Acid Analogues Isolated from Salviae Miltiorrhizae Radix in Rats with Adenine–induced Renal Hypertension", *Phytotherapy Research,* 9:105–109 (1995).

Yokozawa, T., et al., "Haemodynamic Effects of Magnesium Lithospermate B in Rats with Renal Failure", *Phytotherapy Research,* 6:194–199 (1992).

Shigematsu, T., et al., "Inhibition of collagen hydroxylation by lithospermic acid magnesium of collagen hydroxylation by lithospermic acid magnesium salt, a novel compound isolated from *Salviae miltiorrhizae"Biochem Acta,* 1200(1):79–83 (1994).

Yokozawa, T., et al., "Effects of Magnesium Lithospermate B on Urinary Excretion of Arachidonate Metabolites in Rats with Renal Failure", *Chem. Pharm. Bull (Tokyo),* 37(10):2766–2769 (1989).

Yokozawa, T., et al., "Chronic Effect of Salviae Miltiorrhizae Radix on Renal Tissue Blood Flow and Blood Pressure in Uremic Rats", *Chemical & Pharmaceutical Bullentin,* 35(3):1157–1161 (1987).

Chung, H.Y., et al., "The Promoting Action of Magnesium Lithospermate B on the Kinin–Prostaglandin $E_2$ System in the Kidney", *Pharmacology & Toxicology,* 76:240–244 (1995).

Chung, H.Y., et al., "Acute Effect of Extract from Salviae Miltiorrhizae Radix on Renal Function in Renal Failure Rats", *Chem Pharm Bull,* 36(1):274–278 (1988).

Chung, H.Y., et al., "Effect of Extract from Salviae Miltiorrhizae Radix on Uremic Rats", *Chem Pharm Bull,* 34(9):3818–3822 (1986).

Yokozawa, T., et al., "Potentiating Effect of Converting Enzyme Inhibitor Captopril to the Renal Responses of Magnesium Lithospermate B in Rats with Adenine–Induced Renal Failure", *Chem Pharm Bull,* 39(3):732–736 (1991).

TREATMENT OF DIABETIC NEPHROPATHY AND MICROALBUMINURIA

BACKGROUND OF THE INVENTION

Diabetic nephropathy accounts for approximately half of the patients receiving long-term renal dialysis and end-stage renal disease (Robbins, S. L., et al., "Basic Pathology", 2nd ed., Ch. 13, W. B. Saunders, Philadelphia, Pa. (1976)). Microalbuminuria is a predictor of diabetic nephropathy (Abbott, K. C. et al., *Arch. Intern. Med.* 154:146–153 (1994); Neil, A. et al., *Diabetes Care* 16:996–1003 (1993); Mattock, M. B. et al., *Diabetes* 41:736–741 (1992)). Clinical management strategies, such as aggressive glycemia treatments, anti-hypertensive therapies and low-protein diets, can moderate symptoms of diabetic nephropathy and microalbuminuria. However, such treatments must be meticulously monitored in patients, can be costly, are frequently associated with adverse side effects, and are typically less effective in patients where the diabetic nephropathy condition or microalbuminuria has been present for some time and where protein intake is difficult to control. Thus, there is a need to develop new, improved, and effective methods of treatment for diabetic nephropathy and microalbuminuria.

SUMMARY OF THE INVENTION

The present invention relates to a method of treating diabetic nephropathy or microalbuminuria in an individual.

In one embodiment, the method includes administering a Salviae Miltiorrhizae Radix herb, a Salviae Miltiorrhizae Radix mimic, or component thereof, to a diabetic individual exhibiting diabetic nephropathy.

In another embodiment, the method further includes the step of forming an extract of the Salviae Miltiorrhizae Radix herb or the Salviae Miltiorrhizae Radix mimic. The extract is administered to the diabetic individual exhibiting diabetic nephropathy. In a preferred embodiment, the extract is formed by boiling the Salviae Miltiorrhizae Radix or Salviae Miltiorrhizae Radix mimic.

In still another embodiment, the method includes determining the level of protein in urine of a diabetic individual, comparing the level of protein in urine of the diabetic individual with a control level, and administering a Salviae Miltiorrhizae Radix herb, a Salviae Miltiorrhizae Radix mimic or component thereof to lower the level of protein in urine of the diabetic individual to about that of the control level. In a preferred embodiment, an extract of the Salviae Miltiorrhizae Radix herb or Salviae Miltiorrhizae Radix mimic is administered to the diabetic individual.

Another embodiment includes administering a salt of lithospermic acid to the diabetic individual exhibiting diabetic nephropathy.

In yet another embodiment, the invention includes determining the level of protein in urine of a diabetic individual, comparing the level of protein in urine with a control level, and administering a salt of lithospermic acid to lower the level of protein in urine of the diabetic individual to about that of the control level. In a preferred embodiment, the salt of lithospermic acid used in the method of the invention is magnesium lithospermate B or magnesium lithospermate B mimic.

The methods of the invention can be used to treat diabetic nephropathy in a noninsulin-dependent diabetic individual and an insulin-dependent diabetic individual.

The invention also relates to treating microalbuminuria in an individual by administering a Salviae Miltiorrhizae Radix herb, a Salviae Miltiorrhizae Radix mimic, or component thereof, to the individual.

In another embodiment, the method includes forming an extract of a Salviae Miltiorrhizae Radix herb or a Salviae Miltiorrhizae Radix mimic and administering the extract to an individual exhibiting microalbuminuria. In a preferred embodiment, the extract is formed by boiling the Silviae Miltiorrhizae Radix herb or Salviae Miltiorrhizae Radix mimic.

In an additional embodiment of the invention, the level of albumin in urine of the individual exhibiting microalbuminuria is determined and compared to the level of albumin in urine with a control level. A Salviae Miltiorrhizae Radix herb or a Salviae Miltiorrhizae Radix mimic or component thereof is administered to the individual to restore the level of albumin in urine in the individual exhibiting microalbuminuria to about that of the control level. In another embodiment, the method further includes the step of forming an extract of the Salviae Miltiorrhizae Radix herb or Salviae Miltiorrhizae Radix mimic. In a preferred embodiment, the extract is formed by boiling the Salviae Miltiorrhizae Radix herb or the Salviae Miltiorrhizae Radix mimic.

Another embodiment includes treating microalbuminuria by administering a salt of lithospermic acid to an individual exhibiting microalbuminuria.

In yet another embodiment, the method of treating microalbuminuria in an individual includes determining the level of albumin in urine of the individual, comparing the level of albumin in urine with a control level, and administering a salt of lithospermic acid to the individual to restore the level of albumin in urine in the individual exhibiting microalbuminuria to about that of a control level.

The invention described herein provides a method for treating diabetic nephropathy and microalbuminuria. Advantages of the claimed invention include, for example, the treatment of diabetic nephropathy or microalbuminuria in an individual in a cost effective manner and without significant adverse side-effects, especially in individuals who have had the condition for an extended time and where clinical management strategies are difficult to implement. The claimed methods provide an efficient way to treat and reduce the severity of kidney disease and, ultimately, renal failure in diabetic patients.

Thus, treatment with the Salviae Miltiorrhizae Radix herb can potentially halt, reverse or diminish the progression of diabetic nephropathy or microalbuminuria, thereby increasing quality of life and life expectancy, without invasive medical interventions such as renal dialysis and kidney transplants.

DETAILED DESCRIPTION OF THE INVENTION

Figure 1:
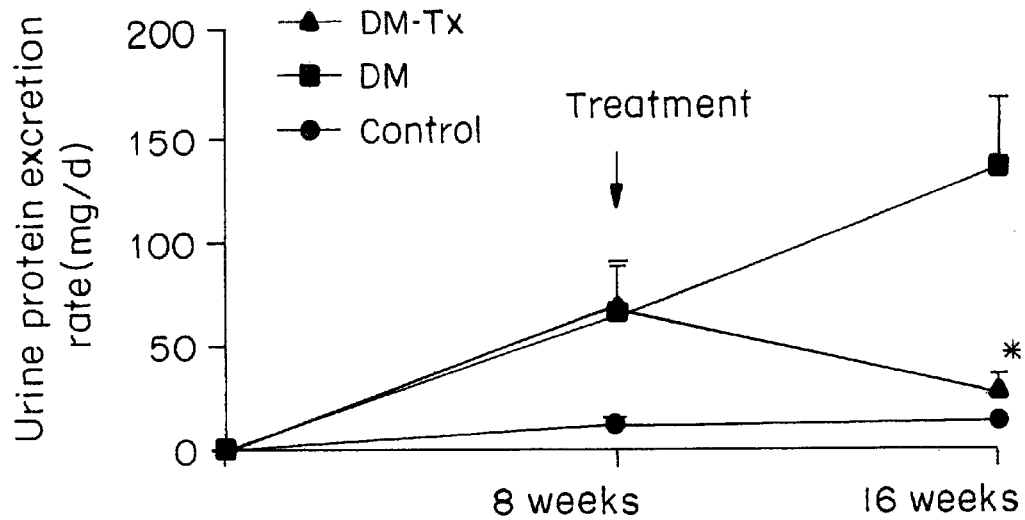
FIG. 1 depicts the daily (d) urinary protein excretion rate (mg/d) in nondiabetic control (-●-), untreated diabetic (-■-DM) and diabetic rats treated with a salt of lithospermic acid (-▲-DM-Tx). Treatment with a salt of lithospermic acid was initiated 8 weeks after induction of diabetes and is indicated by the arrow.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to the discovery that treatment with the herb Salviae Miltiorrhizae Radix ("the herb") decreases protein levels in urine of diabetic individuals exhibiting diabetic nephropathy. In particular, a boiled extract of the herb has been found to decrease the total protein present in urine of diabetic patients exhibiting diabetic nephropathy.

"Diabetic nephropathy" refers to a disease or disorder of the kidney that compromises the function of the kidney (e.g., to prevent leakage of protein) consequent to, or as part of, a diabetic condition. Diabetic nephropathy can result from a primary pathology of the kidney or another organ which adversely affects the ability of the kidney to perform biological functions. Thus, diabetic nephropathy can be the direct and/or indirect effect of disease on kidneys.

Diabetic nephropathy can be indicated by urinary protein levels in a diabetic individual greater than about 0.1 5 g/24 h. Using standard medical criteria, one of skill in the art would be capable of diagnosing a diabetic individual exhibiting diabetic nephropathy.

A "diabetic individual" can be an individual with noninsulin-dependent diabetes mellitus (NIDDM), or an individual with insulin-dependent diabetes mellitus (IDDM). As used herein, an "individual" is any mammal. A mammal can be a rodent (such as rats, mice or guinea pigs), domesticated animal (such as dogs or cats), ruminant animal (such as horses, cows) or a primate (such as monkeys or humans). Human individuals are also referred to herein as "patients."

The term IDDM can be used interchangeably with Type I Diabetes and NIDDM can be considered equivalent to Type II Diabetes. ("Principles of Internal Medicine", Fauci, A. S., et al., eds., 14th ed., McGraw-Hill, New York, N.Y. (1998)). IDDM can occur during the first two decades of life or can develop at any age in the individual. IDDM is characterized by polyuria, increased appetite, weight loss, low plasma insulin levels and episodic ketoacidosis, destruction of beta pancreatic cells, insulin therapy and dietary regulation. NIDDM is often a milder form of diabetes with a gradual onset, usually in obese individuals, over the age of 35. Plasma insulin levels in NIDDM are normal to high but relatively low in relation to plasma glucose levels, and ketoacidosis is rare. However, hyperosmolar coma can occur. NIDDM can respond to dietary regulation or oral hypoglycemic agents, but diabetic complications and degenerative changes can develop. Established clinical criteria to classify diabetic patients as insulin-dependent and noninsulin-dependent are well-known. (See, for example, World Health Organization, WHO Expert Committee on Diabetes Mellitus. Second Report. Geneva. Tech. Rep. No. 646 (1980)).

The Salviae Miltiorrhizae Radix herb is widely available. The herb has been used to treat human conditions such as menstrual disorders, menostatis, menorrhagia, insomnia, blood circulation diseases, angina pectoris, inflammation and certain kidney diseases (Pharmacopoeia Committee of the Health Ministry of the People's Republic of China (ed.), "Pharmacopoeia of People's Republic of China" Vol. I, pages 62–63, Guangdong Scientific Technologic Publisher, Guangdong, (1995); Chiang Su New Medicinal College (ed.), "Dictionary of Chinese Crude Drugs." Shanghai Scientific Technologic Publisher, Shanghai, pages 478–482 (1977); Namba T., "The Encyclopedia of Wakan-Yaku (Traditional Sino-Japanese Medicines) with Color Pictures" Vol. I, pages 24–25, Hoikusha Publishing Co., Ltd., Osaka, (1993); Yokozawa, T., et al., *Nippon Jinzo Gakkai Shi* 37:105–111 (1995); Yokozawa, T., et al., *Nippon Jinzo Gakkai Shi* 32:893–898 (1990); Yokozawa, T., et al., *Nippon Jinzo Gakkai Shi* 31:1091–1098 (1989); Guoji, Y., et al., *Phytotherapy Research* 8:337–341 (1994); Jin, H. J., et al., *J. Chinese Materia Medica* (China) 22:236–238 (1997); Kanou, K., et al., JP 07048265 (1995); Yokozawa, T., et al., *Natural Medicine* 51: 287–292 (1997), the teachings of all of which are incorporated herein in their entirety). The herb is safe for human consumption.

The term "Salviae Miltiorrhizae Radix" herb can be used interchangeably with the terms "Salviae Miltiorrhizae Bunge"; "dry root and rhizome of Salviae Miltioriza Bunge"; and "Danshen."

A "Salviae Miltiorrhizae Radix mimic" is an herb which exhibits similar biological activity to the Salviae Miltiorrhizae Radix herb as described herein. "Biological activity" here refers to the ability of the Salviae Miltiorrhizae Radix herb to alleviate a symptom or characteristic associated with diabetic nephropathy in a diabetic individual (e.g., decrease urinary protein). Thus, a "Salviae Miltiorrhizae Radix mimic" reduces the severity of at least one symptom associated with diabetic nephropathy, similar to that observed following the administration of the Salviae Miltiorrhizae Radix herb (e.g., decreased protein in the urine).

An "amount effective," when referring to the amount of the herb or Salviae Miltiorrhizae Radix mimic, is defined as that amount, or dose, of the herb that, when administered to a diabetic individual exhibiting diabetic nephropathy, is sufficient for therapeutic efficacy (e.g., an amount sufficient to reduce the level of protein in urine in a diabetic individual exhibiting diabetic nephropathy).

In one embodiment, the herb or Salviae Miltiorrhizae Radix mimic is administered in a single dose. In another embodiment, the herb or Salviae Miltiorrhizae Radix mimic is administered in multiple doses.

The method of the invention can include administering an aqueous extract (e.g., methanol, ethanol, water) of the herb or Salviae Miltiorrhizae Radix mimic in an amount effective to alleviate diabetic nephropathy in a diabetic individual. In particular, the methods of the invention include administering a boiled aqueous extract.

A "boiled aqueous extract of the herb," also referred to herein as "herbal extract" or "extract," refers to a preparation of the Salviae Miltiorrhizae Radix herb or Salviae Miltiorrhizae Radix mimic obtained by mixing the dry herb or mimic with a solvent (e.g., distilled water, methanol, physiological buffer). The extract is filtered through an appropriate device for separating solid particles from the liquid solvent (e.g., gauze, Whatman filter paper, Nylon 66 membrane filter). The volume of the extract can be reduced by a suitable method (e.g., boiling, reduced pressure, rotatory evaporation, lyophilization). The extract optionally can be further processed (e.g., organic extraction, fractionation on chromatographic matrixes) to yield components (e.g., salts of lithospermic acid, such as magnesium lithospermate B) for use in the methods of the invention.

In a preferred embodiment, an extract is prepared by adding the herb to distilled water at a ratio of about 1:6–2:10 (w/v) and boiling (~1–3 hours) the herb and water mixture at atmospheric pressure until the volume of water is reduced by about 40–80% to produce a "boiled aqueous extract." The boiled aqueous extract is cooled to about room temperature (18–25° C.) and then gravity filtered through a suitable filter. Examples of suitable filters include gauze, a Whatman No. 1 filter, or a Nylon 66 membrane filter. Additionally, or alternatively, the aqueous extract can be filter-sterilized by vacuum filtration by the use of, for example, a Nalgene 0.2 $\mu$m filter unit. The boiled aqueous extract is divided into about three equivalent aliquots and administered to patients three times a day, for example, before breakfast, lunch and dinner. The boiled aqueous extract can be prepared fresh daily. Alternatively, the boiled aqueous extract can be prepared in batches for weekly consumption and stored at 4° C. until use.

Another aspect of the invention relates to determining the level of protein in urine of a diabetic individual exhibiting diabetic nephropathy and comparing the level of protein in the diabetic individual with the level of protein in urine of a control. An extract of the herb is formed and administered to the diabetic individual in an amount effective to lower the level of protein in urine of the diabetic individual to about that of the control level. The levels of protein in the urine can be determined at one or more time points before, during and/or after treatment with the herb or herbal extract.

As defined herein, "control" level means a target level of urinary protein in an individual not exhibiting diabetic nephropathy, matched for age, sex, ethnicity and health history with the diabetic individual to be treated. For example, the control level can be the expected level of urinary protein in an individual. The "expected level" of urinary protein in an individual treated by the methods of the invention can be a level normally expected in an individual not exhibiting the diabetic nephropathy, or can be higher than an individual not exhibiting diabetic nephropathy yet below the level in an individual with diabetic nephropathy. An expected level can also be any level of protein in the urine that is below pretreatment levels. A "target level" of urinary protein can be selected for an individual exhibiting diabetic nephropathy based on the level of protein in the urine of a diabetic individual before that diabetic individual developed diabetic nephropathy, or in comparison to levels observed in individuals not exhibiting diabetic nephropathy.

The herbal extract is administered to the diabetic individual, and then urinary protein levels are determined and compared to the control level. Additional doses of the herbal extract can be administered to the diabetic individual, as needed, to lower urinary levels based on comparison to a control level. Protein levels in urine of the individual being treated with the herb or herbal extract can be compared to a control level to determine the progress of treatment and need for further doses.

Thus, the levels of protein in urine after treatment are about the levels of a control when the levels observed after treatment approach target levels, or are higher or lower than levels observed in individuals not exhibiting diabetic nephropathy. The levels of protein in urine of an individual after treatment with the herb, herbal extract or mimic are below pretreatment levels.

Typically the levels of protein in urine are determined using routine assays well known to one of skill in the art. Suitable methods include dipstick, immunoprecipitation, turbidimetric (e.g., sulphosaliclic acid, tricholoracetic, benzethonium chloride) assays, dye-binding (e.g., Coomassie Blue, Ponceau) assays, Biuret (e.g., precipitation with Tsuchiya reagent) assays and Folin-Lowry assays. ("Oxford Textbook of Clinical Nephrology" eds. Davison, A. M., et al., 2nd edition, Oxford University Press, New York, N.Y. (1998); "Primer on Kidney Diseases" ed., Greenberg, A., 2nd edition, Academic Press, New York, N.Y. (1998)).

In another embodiment of the invention, diabetic nephropathy is treated by administering a salt of lithospermic acid to a diabetic individual in an amount effective to alleviate diabetic nephropathy.

The term "salt of lithospermic acid," also referred to herein as "lithospermic acid," is defined herein as a component of a composition obtained by forming an aqueous extract of the Salviae Miltiorrhizae Radix herb or Salviae Miltiorrhizae Radix mimic that is fractionated by chromatography according to modifications of previously described methods. (See, for example, Tanaka, T., et al., *Chem. Pharm. Bull.* 37:340–344 (1989); Yokozawa, T., etal., *Jap. J. Nephrol.* 31:1091–1098 (1989); Yokozawa, T., et al., *Nephron* 75:88–93 (1997), the teachings of all of which are incorporated herein in their entirety). The salt of lithospermic acid can be, for example, a sodium, potassium, calcium, ammonium, magnesium salt or any combination thereof. As shown in the exemplification, a salt of lithospermic acid decreases the protein in urine of individuals suffering from insulin-dependent diabetes and noninsulin dependent diabetes.

An aqueous extract of the Radix Salivae miltiorhizae herb is admixed with an ethanolic solvent followed by organic extraction and chromatography to yield a salt of lithospermic acid. Specifically, the herb is mixed with methanol (50–95%) at a ratio of about 1:3 to 1:10 (w/v) and allowed to remain at room temperature (18–25° C.) for about 2–5 days. The resulting mixture is filtered, for example, by gravity using a Whatman No. 1 filter or by vacuum filtration using a Nylon 66 membrane filter (0.45 $\mu$m) to form a particulate fraction and a liquid extract fraction. The liquid extract fraction, containing the herbal extract, is subjected to reduced pressure (5–10 mmHg, 18–25° C., 15 min-2 hours) to reduce the volume and remove the methanol, thereby forming an aqueous extract. The aqueous extract is sequentially extracted with hexane, diethyl ether, $CH_2Cl_2$ and ethyl acetate (4 times each solvent, 200–400 mL each) to remove soluble organics. The aqueous phase can be concentrated by lyophilization to yield a visible solid material. About 10–30 g of solid material is extracted from about 100 g of Salviae Miltiorrhizae Radix. The resulting solid material is resuspended in a suitable solution such as a buffer (e.g., PBS, HEPES) or chromatographic eluent (e.g., isopropanol/$H_2O$/EtOAc (3:1:3, v/v/v). A salt of lithospermic acid is obtained from the solid material by chromatographic fractionation (e.g., 7 cm diameter×20 cm length, 70–230 mesh $SiO_2$ gel, flow rate of about 10 mL/10 min) employing isopropanol/$H_2O$/EtOAc (3:1:3) as an eluent.

A salt of lithospermic acid is contained in chromatographic fractions ($R_f$ at about 0.50–0.75). The fractions containing the salt of lithospermic acid can be pooled, dialyzed (Mr cutoff 3,500) against distilled water or an appropriate buffer, such as phosphate buffer saline (PBS) or Ringer's solution, for about 24 hours at 4° C. and lyophilized. The yield of a salt of lithospermic acid typically is about 1–2 g per 100 g Salviae Miltiorrhizae Radix herb. The salt of lithospermic acid is resuspended in a suitable buffer (e.g., PBS, HEPES) or medium (e.g., DMEM) in a suitable volume and, when required, concentrated (e.g., filtration, lyophilization) prior to use. The salt of lithospermic acid can be filter-sterilized by use, for example, of a Nalgene filter (0.22 $\mu$m, 0.45 $\mu$m) prior to administration to the individual. The presence of a salt of lithospermic acid in the chromatographic fractions can be confirmed using $^1$H NMR or $^{13}$NMR (Nuclear Magnetic Resonance), mass spectroscopy, mass fragmentation, infrared spectroscopy or other suitable methods well-known to the skilled artisan.

The salt of lithospermic acid generally has a molecular weight of about 700–800 atomic mass units and is a tetramer of caeffic acid. An example of the salt of lithospermic acid employed in the methods of the invention generates fragment ions in APCI-LC-mass spectra of about 500–525 (preferably about 518) m/z, 480–495 (preferably about 492) m/z, 345–360 (preferably about 353) m/z, 315–325 (preferably about 321) m/z, 290–300 (preferably about 295) m/z, 260–275 (preferably about 269) m/z, 190–210 (preferably about 196) m/z, 170–185 (preferably about 178) m/z and 130–145 (preferably about 134) m/z.

The lithospermic acid can also be characterized by infrared spectrum in solid as KBr dispersion containing, for example, H-bonded phenolic OH/aromatic OH at 3400 (bR)/2900 $\lambda$ (cm$^{-1}$); ester carbonyl at 1721 $\lambda$ (cm$^{-1}$); conjugated carbonyl at 1600 $\lambda$ (cm$^{31\ 1}$); carboxylate carbonyl at 1520(s) $\lambda$ (cm$^{-1}$); symmetrical stretching of carboxylate carbonyl at 1400(w) $\lambda$ (cm$^{-1}$) and -0-0- stretching at 1290 $\lambda$ (cm$^{-1}$).

An "amount effective," when referring to the amount of a salt of lithospermic acid, is defined as that amount, or dose, of the salt of lithospermic acid that, when administered to the diabetic individual, is an amount sufficient for therapeutic efficacy (e.g., an amount sufficient to reduce the level of protein in urine in a diabetic individual exhibiting diabetic nephropathy). The salt of lithospermic acid or magnesium lithospermate B can be administered in a single dose or in multiple doses.

In one embodiment, treatment of diabetic individuals with a salt of lithospermic acid decreases total protein levels in urine below those levels observed prior to treatment with the salt of lithospermic acid. In a particular embodiment, the levels of protein in urine following administration of the salt of lithospermic acid can be lowered to about that of a control level.

In a preferred embodiment, the methods of the invention include treating diabetic individuals (e.g., noninsulin-dependent and insulin-dependent) exhibiting diabetic nephropathy with magnesium lithospermate B or a magnesium lithospermate B mimic, extracted from the herb or synthesized by a suitable chemical method. Suitable methods to obtain magnesium lithospermate B from the herb are well-known. (See, for example, Tanaka, T., et al., *Chem. Pharm. Bull.* 37:340–344 (1989); Yokozawa, T., et al., *Jap. J. Nephrol.* 31:1091–1098 (1989); Yokozawa, T., et al., *Nephron* 75:88–93 (1997); Yokozawa T., et al., *Exp. Toxic. Pathol.* 49:343–346 (1997), the teachings of all of which are incorporated herein in their entirety).

A "magnesium lithospermate B mimic" is defined herein as any molecule (e.g., small organic molecule) exhibiting a biological activity similar to magnesium lithospermate B. For example, a magnesium lithospermate B mimic is capable of reducing the severity of at least one symptom associated with diabetic nephropathy, similar to that observed following the administration of magnesium lithospermate B (e.g., decreased proteinuria in a diabetic individual exhibiting diabetic nephropathy). Thus, the administration of a magnesium lithospermate B mimic to an individual exhibiting diabetic nephropathy, can decrease protein levels in urine.

The invention further relates to the use of the Salviae Miltiorrhizae Radix herb or salts of lithospermatic acid (e.g., magnesium lithospermate B), or their mimics, to treat individuals exhibiting microalbuminuria. In a preferred embodiment, the salt of lithospermic acid is magnesium lithospermate B.

The term "microalbuminuria" refers to any disease, disorder, ailment or state of health where urinary albumin is excreted at a rate of about 20–200 $\mu$g/minute or about 30–300 mg/24 hours. (see, for example, Abbott, K. C., et al., *Arch. Internal Med.* 154:146–153 (1994), the teachings of which are incorporated herein by reference in their entirety). Methods to detect and diagnosis microalbuminuria are well known to one of skill in the art and include radioimmunoassays, immunoassays with latex bodies, fluoroimmunoassays, enzyme immunoassays, agglutination inhibition, immunoturbidimetry, immunonephelometry and radial immunodiffusion assays. (Keen, H. et al., *Lancet* 2:913–916 (1968); Silver, A. et al., *Clin. Chem* 32: 1303–1306 (1986); Close, C. et al., *Diabet. Med.* 4:491–492 (1987); Harmoinen, A. et al., *Clin. Chim. Acta* 166:85–89 (1987); Marre, M. et al., *Clin. Chem.* 33:209–213 (1987); McCormik, C. P. et al., *Ann. Clin. Lab Sci.* 19:944–951 (1989); Cambiaso, C. L. et al., *Clin. Chem.* 34:416–418 (1988); Niwa, T. et al., *Clin. Chim. Acta* 186:391–396 (1990), the teachings of all of which are incorporated herein in their entirety). The levels of albumin or total protein in urine before and after treatment with the herb, Salviae Miltiorrhizae Radix mimic, salt of lithospermic acid, magnesium lithospermate B or magnesium lithospermate B mimic can be determined and the frequency or amount of doses required to alleviate microalbuminuria can be adjusted as needed for each individual undergoing treatment. Since microalbuminuria is associated with diabetic nephropathy in diabetic individuals (Mattock, M. B., et al., *Diabetes* 41:736–741 (1992); Neil, A., et al., *Diabetes Care* 16:996–1003 (1993); Abbott, K. C., et al., *Arch. Intern. Med.* 154:146–153 (1994), the teachings of all of which are incorporated herein in their entirety) it is expected that the methods of the invention can be employed to halt the progression of microalbuminuria and, thus, prevent development of diabetic nephropathy.

An aqueous extract of the herb or magnesium lithospermate B can be administered to an individual exhibiting microalbuminuria in an amount effective to alleviate microalbuminuria. The amount effective to alleviate microalbuminuria can be an amount of the herb, herbal extract, Salviae Miltiorrhizae Radix mimic, magnesium lithospermate B, or magnesium lithospermate B mimic that restores the levels of albumin in urine. In a preferred embodiment, the levels of albumin in urine are restored to levels of about that in a control individual. The term "restore" refers to returning the albumin levels in urine to the levels observed before the individual developed microalbuminuria or to levels of about that observed in a control individual. The herbs or salt of lithospermic acid can be used to prevent progression of the microalbuminuria.

A "control" level, when referring to the treatment of individuals exhibiting microalbuminuria, is defined as described above for diabetic nephropathy except the control level refers to a level of urinary albumin, rather than a level of total protein as described in individuals exhibiting diabetic nephropathy.

It is also envisioned that other components of the chromatographic fractions containing a salt of lithospermic acid or magnesium lithospermate B can be used in the methods of the invention to alleviate diabetic nephropathy in a diabetic individual or to alleviate microalbuminuria in an individual.

The biological activity of other components of chromatographic fractions containing magnesium lithospermate B or a salt of lithospermic acid can be, for example, assessed using in vivo and in vitro bioassays. By way of illustration, the biological activity can be evaluated in vitro, using cultured mesangial cells, by the ability to decrease glucose-induced increases in protein kinase C activity; TGF-β1 synthesis and secretion; fibronectin synthesis; the phosphorylation of ERK, or any combination thereof as described below. Alternatively, or additionally, the biological activity can be evaluated in vivo by its ability to decrease urinary protein excretion rates in a diabetic individual exhibiting diabetic nephropathy or to restore urinary albumin levels in individuals exhibiting microalbuminuria to control levels.

It is also envisioned that portions of the salt of lithospermic acid or magnesium lithospermate B can be used in the methods of the invention. A "portion" of the salt of lithospermic acid or magnesium lithospermate B, as used herein, refers to any part of magnesium lithospermate B capable of alleviating any of the symptoms of diabetic nephropathy, such as decreasing protein in urine in a diabetic individual exhibiting diabetic nephropathy, restoring urinary albumin levels to control levels in an individual exhibiting microalbuminuria or preventing the onset of diabetic nephropathy in an individual exhibiting microalbuminuria. For example, a portion of magnesium lithospermate B can be a metabolite of magnesium lithospermate B.

It is also envisioned that biologically active salts of lithospermic acid, magnesium lithospermate B or portions thereof can be designed and produced by synthetic techniques known to those of skill in the art. The synthetic molecules can be based, for example, on the known structure of magnesium lithospermate B and its metabolites. The synthetic magnesium lithospermate B, portions of magnesium lithospermate B or metabolites of magnesium lithospermate B would possess biological activity (e.g., decrease elevated levels of protein in urine of individuals exhibiting diabetic nephropathy or restoring urinary albumin levels in individuals exhibiting microalbuminuria to about control levels) similar to the biological activity of salts of lithospermic acid or magnesium lithospermate B obtained from the Salviae Miltiorrhizae Radix herb. The synthetic salts of lithospermic acid, magnesium lithospermate B, their metabolites or portions can possess a "biological advantage" over the salts of lithospermic acid or magnesium lithospermate B extracted from the herb with respect to one, or more, of the following properties: solubility, stability, and susceptibility to hydrolysis and proteolysis.

The methods of the invention can also decrease the production and secretion of extracellular matrix proteins and cell signal molecules implicated in glomerular basement membrane accumulation in individuals exhibiting diabetic nephropathy. For example, a decrease in fibronectin synthesis and secretion is accompanied by a decrease in the activity of protein kinase C; and levels of TGF-β, phosphorylated ERK and MEK in mesangial cells.

In addition, or as an alternative to monitoring protein levels in urine (e.g., albumin, or total protein), other physiological parameters can be monitored during the course of treatment to determine the effect of the herb, Salviae Miltiorrhizae Radix mimic, salt of lithospermic acid or magnesium lithospermate B. The physiological parameters can be, for example, creatinine, blood urea nitrogen levels, or any combination thereof. The physiological parameters can be assessed at one or more time points before, during, and/or after administration of the herb, a Salviae Miltiorrhizae Radix mimic, a salt of lithospermic acid or magnesium lithospermate B. A variety of suitable assays to assess physiological parameters are known to those of skill in the art.

The methods of the present invention can be accomplished by the administration of the herbal extract, salt of lithospermic acid, magnesium lithospermate B or mimics of the invention by enteral or parenteral means. Specifically, the route of administration is by oral ingestion (e.g., drink, tablet, capsule form) or intramuscular injection of the herbal extract, salt of lithospermic acid or magnesium lithospermate B. Other routes of administration as also encompassed by the present invention including intravenous, intraarterial, intraperitoneal, or subcutaneous routes, and nasal administration. Suppositories or transdermal patches can also be employed.

The herbal extract, salt of lithospermic acid, magnesium lithospermate B or mimics of the invention can be administered alone or can be coadministered to the patient. Coadminstration is meant to include simultaneous or sequential administration of the extract, salt of lithospermic acid, magnesium lithospermate B, or mimics individually or in combination. Where the extract, salt of lithospermic acid or magnesium lithospermate B are administered individually it is preferred that the mode of administration is conducted sufficiently close in time to each other (for example, administration of the extract close in time to administration of the salt of lithospermic acid) so that the effects on diabetic nephropathy or microalbuminuria are maximal. It is also envisioned that multiple routes of administration (e.g., intramuscular, oral, transdermal) can be used to administer the herb, extract, salt of lithospermic acid, magnesium lithospermate B, or any combination thereof.

The herbal extracts, salt of lithospermic acid, or magnesium lithospermate B can be administered alone or as admixtures with conventional excipients, for example, pharmaceutically, or physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxillary agents such as lubricants, preservatives, stabilizers, wetting agents, emulsifiers, salts for influencing osmotic pressure, buffers, coloring, and/or aromatic substances and the like which do not deleteriously react with the herb, herbal extract, salt of lithospermic acid or magnesium lithospermate B. The preparations can also be combined, when desired, with other active substances to reduce metabolic degradation. A preferred method of administration of the herbal extract is oral administration, such as a drink. A preferred method of administration for the salt of lithospermic acid or magnesium lithospermate B is as an intramuscular injection. The herbal extract, salt of magnesium lithospermate or magnesium lithospermate B alone, or when combined with an admixture, can be administered in a single or in more than one dose over a period of time to confer the desired effect (e.g., alleviate diabetic nephropathy or microalbuminuria).

When parenteral application is needed or desired, particularly suitable admixtures for the herbal extract, salt of lithospermic acid or magnesium lithospermate B are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The herbal extract, salt of lithospermic acid or magnesium lithospermate B can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309 the teachings of which are hereby incorporated by reference.

The dosage and frequency (single or multiple doses) administered to an individual can vary depending upon a variety of factors, including the duration of diabetic nephropathy or microalbuminuria, whether the individual suffers from insulin-dependent or noninsulin-dependent diabetes, and its route of administration; size, age, sex, health, body weight, body mass index, and diet of the recipient; nature and extent of symptoms of the disorder being treated (e.g., diabetic retinopathy), kind of concurrent treatment (e.g., insulin), complications from diabetic nephropathy, microalbuminuria, or other health-related problems. Other therapeutic regimens or agents can be used in conjunction with the methods and herbal extracts of the present invention. For example, the administration of the herbal extract can be accompanied by a low-protein diet. Adjustment and manipulation of established dosages (e.g., frequency and duration) are well within the ability of those skilled in the art.

The present invention is further illustrated by the following examples, which are not intended to be limiting in any way.

EXEMPLIFICATION

Example 1

PREPARATION OF THE HERBAL EXTRACT AND ADMINISTRATION OF THE EXTRACT TO DIABETIC INDIVIDUALS

The Chinese herb (150 g) Danshen (Salviae Miltiorrhizae Radix) was boiled in 900 mL of distilled water for approximately two hours to reduce the total volume of liquid to approximately 450 mL. The boiled extract was allowed to cool at room temperature, gravity filtered through several layers of gauze, divided into three equal aliquots and stored at 4° C. until use. Approximately 150 mL of the extract was administered three times daily, for a four week treatment period, to each patient as a drink before breakfast, lunch and dinner.

Example 2

TREATMENT OF DIABETIC NEPHROPATHY WITH THE HERBAL EXTRACT

Twenty Chinese patients exhibiting diabetic nephropathy participated in the study. The patients ranged in age from 42–69 years and consisted of 12 males and 8 females. (Table 2).

All patients had NIDDM according to the criteria established by the World Health Organization (WHO Expert Committee on Diabetes Mellitus. Second Report. Geneva. Tech. Rep. No. 646 (1980)). Diabetic nephropathy was indicated by urinary protein levels >0.15 g/24 h. None of the patients had a history or diagnosis of any other kidney disease that would contribute to urinary protein levels >0.15 g/24 h. Two patients had diabetic retinopathy, one had microaneurysms and one had cotton-wool spot.

Patients drank boiled extracts (~150 mL) of the herb, described in Example 1, three times a day, before breakfast, lunch and dinner. All patients were simultaneously orally treated with the noninsulin hypoglycemic agent gliquidone. Blood and urine samples were obtained from each patient prior to treatment with the boiled extract and following 4 weeks of treatment with the herb. Blood and urine samples were collected for, for example, blood glucose levels, blood urea nitrogen levels and total urinary protein employing standard, art-recognized protocols (such as Chemstrip and Accu-Check III blood monitor system of Boehringer Mannheim Biochemicals., Indianapolis, Ind., to measure blood glucose levels).

The effects of treatment with the herbal extract on several indices (urinary protein, hemoglobin A1c (HbA1c), fasting plasma glucose (FPG), blood urea nitrogen (BUN), and creatinine levels are shown in Tables 2–3. These data are expressed as the mean±SD for the twenty determinations. Statistically significant differences between mean values before and after treatment were determined using the Student's t-test.

As shown in Tables 2 and 3, the total urinary protein levels (grams/24 hours) significantly declined following four weeks of treatment with a boiled extract of the Salviae Miltiorrhizae Radix herb. Urinary protein levels decreased from 0.96±0.39 g/24 h before treatment to 0.42±0.14 g/24 h following four weeks of treatment with the herbal extract.

No statistically significant differences in fasting plasma glucose and blood urea nitrogen levels (Table 3); systolic and diastolic blood pressure (BP); and creatinine and hemoglobin (Hb) A1c levels (Table 2) were observed after treatment with the herbal extract.

These data show that methods of the invention provide a convenient, cost-effective, and efficacious means to ameliorate the degenerating effects of diabetic nephropathy.

TABLE 2

Physiological Parameters Before and After Treatment

| | Before Treatment | After Treatment | p value |
|---|---|---|---|
| N | 20 | | |
| Sex (M/F) | 12/8 | | |
| Age (years) | 55.20 ± 8.17 | | |
| FPG (mg/dl) | 139.94 ± 24.42 | 138.24 ± 23.24 | >0.05 |
| HbAlc (%) | 7.27 ± 1.69 | 7.33 ± 1.59 | >0.05 |
| Total Cholesterol (mmol/L) | 4.91 ± 0.93 | 4.25 ± 0.68 | <0.05 |
| BUN (mg/dl) | 16.04 ± 6.43 | 15.84 ± 6.34 | >0.05 |
| Creatinine (mg/dl) | 0.95 ± 0.37 | 0.93 ± 0.34 | >0.05 |
| Systolic BP (mmHG) | 130.85 ± 6.77 | 129.15 ± 6.94 | >0.05 |
| Diastolic BP (mmHg) | 83.00 ± 5.02 | 81.25 ± 4.79 | >0.05 |
| Urine Protein (g/24 h) | 0.96 ± 0.39 | 0.42 ± 0.14 | <0.01 |

TABLE 3

Urinary Protein, Bloods Urea Nitrogen (BUN) and Creatinine Levels Before (Pre-Tx) and After (Post-Tx) Treatment

| Patient No. | Urine Protein (grams/24 hours) | | BUN (mg/dl) | | Creatinine (mg/dl) | |
|---|---|---|---|---|---|---|
| | Pre-Tx | Post-Tx | Pre-Tx | Post-Tx | Pre-Tx | Post-Tx |
| No. 1 | 1.3 | 0.41 | 5.7 | 6.8 | 1.4 | 1.2 |
| No. 2 | 0.48 | 0.61 | 7.8 | 7.9 | 0.6 | 0.6 |
| No. 3 | 1.5 | 0.5 | 18.6 | 18.6 | 0.7 | 0.5 |
| No. 4 | 0.82 | 0.24 | 17.4 | 19.6 | 0.8 | 1.2 |
| No. 5 | 1.49 | 0.57 | 21.5 | 20.9 | 0.9 | 0.9 |
| No. 6 | 0.73 | 0.62 | 20.4 | 18.4 | 1.2 | 1.1 |
| No. 7 | 1.48 | 0.55 | 19 | 24.7 | 1.5 | 1.3 |
| No. 8 | 0.85 | 0.48 | 9.4 | 5.7 | 1.3 | 1.5 |
| No. 9 | 0.97 | 0.29 | 21.4 | 19.4 | 0.5 | 0.9 |
| No. 10 | 0.42 | 0.28 | 16.8 | 18.4 | 0.4 | 0.8 |
| No. 11 | 0.56 | 0.23 | 15.4 | 10.9 | 1.2 | 0.8 |
| No. 12 | 1.5 | 0.31 | 14.3 | 8.7 | 1.5 | 0.1 |
| No. 13 | 0.4 | 0.22 | 13.5 | 9.7 | 0.8 | 1.3 |
| No. 14 | 1.3 | 0.27 | 11.7 | 18.6 | 0.8 | 0.8 |
| No. 15 | 1.28 | 0.51 | 6.5 | 14.5 | 1.3 | 1.2 |
| No. 16 | 0.62 | 0.37 | 25.0 | 24.6 | 0.7 | 1.1 |
| No. 17 | 0.57 | 0.6 | 24.5 | 22.7 | 1.4 | 0.6 |
| No. 18 | 0.86 | 0.44 | 23.7 | 20.4 | 1.0 | 1.2 |
| No. 19 | 1.27 | 0.42 | 22.3 | 19.5 | 0.6 | 0.8 |
| No. 20 | 1.08 | 0.54 | 5.9 | 6.7 | 0.4 | 0.7 |
| Mean | 0.957 | 0.423 | 16.04 | 15.835 | 0.95 | 0.93 |
| SD | 0.393 | 0.138 | 6.43 | 6.338 | 0.372 | 0.337 |
| Pre-Tx vs. Post-Tx | $4.5 \times 10^{-6}$ | | 0.920 | | 0.847 | |

Example 3

PREPARATION OF A SALT OF LITHOSPERMIC ACID

A salt of lithospermic acid was obtained from an aqueous extract of the herb using the following modification of previously described protocols. Salviae Miltiorrhizae Radix (100 g) was mixed with 80% methanol (800 mL) at room temperature for 3 days. After removal of the insolubles by gravity filtration through gauze, the MeOH was removed from the liquid under reduced pressure. The water layer of the filtrate was sequentially extracted with hexane, diethyl ether, $CH_2Cl_2$ and ethyl acetate (300 mL×4 each). The resulting aqueous layer was lyophilized to yield a solid material (30 g). The salt of lithospermic acid was obtained from the lyophilized material by chromatography with a $SiO_2$ matrix employing isopropanol/$H_2O$/EtOAc (3:1:3, v/v/v) as an eluent. The yield of the salt of lithospermic acid was about 1.01 g from about 100 g of Salviae Miltiorrhizae Radix.

Example 4

TREATMENT OF DIABETIC RATS WITH A SALT OF LITHOSPERMIC ACID DECREASED URINARY PROTEIN EXCRETION RATES

Sprague-Dawley rats (3–4 months of age, 250–300 g) were housed individually in sterile microisolator cages in a Specific Pathogen Free animal care facility. Rats were fed standard Rat chow and water was available ad libitum. Animals were maintained in temperature (25° C.) and humidity (40%) controlled rooms with a 12-h light/12 h dark cycle.

Rats were randomly assigned to three experimental groups: Group I, nondiabetic control (n=10), Group II, untreated diabetic (n=10); and Group III, salt of lithospermic acid-treated diabetic (n=10). Insulin dependent diabetes was induced by a single intravenous injection of freshly prepared streptozotocin (STZ) (50 mg/kg in 0.1 M citrate buffer, pH 4.5) (Schmidt, R. E., et al., *Diabetes* 45(3):284–290 (1996)). A rat was considered diabetic when the nonfasting plasma glucose level was greater than about 17 mmol/L, 3 days following injection of STZ. Eight weeks following the administration of STZ, animals were treated with a salt of lithospermic acid by intramuscularly injections once daily (20 mg salt of lithospermic acid/kg body weight) for 8 weeks.

Body weights were recorded weekly before and throughout the treatment period. Twenty-four hour urine and glycosylated hemoglobin levels were determined at 8, 12 and 16 weeks after injection of STZ. Urine samples were centrifuged (3000 rpm for 10 min) and the supernatant analyzed for creatinine and protein levels using standard techniques (Matsuo, Y., et al., *Pharmacology* 50:1–8 (1995)).

The administration of STZ induced diabetes in rats (Table 4). Blood glucose levels were significantly elevated in STZ-treated animals (Table 4). As shown in FIG. 1, treatment (-▲-DM-Tx) of diabetic rats with a salt of lithospermic acid significantly ($p<0.001$) lowered urinary protein levels compared to untreated diabetic (-■-DM) rats. The levels of protein in urine of salt of lithospermic acid-treated diabetic rats approached the levels observed in control, nondiabetic rats (FIG. 1).

Treatment with a salt of lithospermic acid did not significantly lower blood glucose levels in diabetic rats. (Table 4). The plasma levels of glycated hemoglobin were significantly higher and body weights significantly lower in diabetic rats compared to nondiabetic rats. The plasma levels of several physiological parameters in nondiabetic animals (e.g., BUN, Uric Acid, Cholesterol, Albumin) were similar to diabetic animals (Table 4), whereas certain blood cell parameters (e.g., hemoglobin (hb) Alc, percentage of reticulocytes and white blood cells) were altered in diabetic animals (Table 5). Therefore, the administration of a salt of lithospermic acid, derived from an extract of the Salviae Miltiorrhizae Radix herb, alleviates symptoms associated with diabetic nephropathy (e.g., elevated protein in urine) without altering other physiological parameters.

TABLE 4

Effect of a salt of lithospermic acid on physiological parameters in STZ-induced diabetic rats

|  | GROUP A<br>Salt of<br>lithospermic acid-<br>Treated Diabetic | GROUP B<br>Untreated<br>Diabetic | GROUP C<br>Non-Diabetic<br>Control |
| --- | --- | --- | --- |
| Serum Protein (g/dl) | 6.28 ± 0.54 | 6.48 ± 0.71 | 6.15 ± 1.1 |
| Albumin (g/dl) | 1.75 ± 0.31 | 1.63 ± 0.30 | 1.83 ± 0.38 |
| BUN (mg/dl) | 28.1 ± 5.32 | 30.3 ± 4.0 | 22.35 ± 4.81 |
| Creatinine (mg/dl) | 0.6 ± 0.12 | 0.55 ± 0.06 | 0.55 ± 0.06 |
| Uric Acid (mg/dl) | 1.6 ± 1.07 | 3.03 ± 1.89 | 1.68 ± 1.73 |
| GOT (U/L) | 239 ± 157 | 213 ± 110 | 277 ± 252.34 |
| GPT (U/L) | 102.75 ± 73.74 | 129 ± 82.87 | 110 ± 104 |
| r-GTP (U/L) | 2.75 ± 2.75 | 2 ± 2.16 | 1 ± 0.82 |
| Cholesterol (mg/dl) | 47 ± 7.35 | 76.75 ± 42.11 | 49.5 ± 11.15 |
| Bilirubin (mg/dl) | 1.14 ± 1.10 | 0.98 ± 1.14 | 1.30 ± 1.78 |
| D. Bil (mg/dl) | 0.67 ± 0.7 | 0.73 ± 1.02 | 0.73 ± 1.04 |
| Glucose (mg/dl) | 508.5 ± 160.4 | 611 ± 32.78 | 122 ± 14.5 |
| Na (mmol/L) | 130.3 ± 6.24 | 129 ± 11.3 | 131 ± 8.246 |
| K (mmol/L) | 19.53 ± 12.8 | 23.7 ± 11.51 | 24 ± 16.6 |
| CI (mmol/L) | 101.5 ± 2.65 | 101.75 ± 3.59 | 105 ± 0.82 |

TABLE 5

Effect of a salt of lithospermic acid on blood cells

|  | Salt of Lithospermic Acid-Treated | Diabetic Untreated | NonDiabetic Control |
| --- | --- | --- | --- |
| HbAlc (%) | 8.59 ± 1.59** | 9.04 ± 0.39** | 3.8 ± 0.16 |
| HCT (%) | 37.44 ± 3.13 | 39.17 ± 2.78 | 35.80 ± 2.17 |
| Hb (g/dl) | 14.44 ± 0.87 | 14.77 ± 0.73 | 14.30 ± 0.56 |
| WBC × 10(3) | 11.95 ± 4.66 | 7.03 ± 2.70 | 10.50 ± 2.56 |
| MCH (pg) | 21.13 ± 0.69 | 21.24 ± 0.62 | 21.82 ± 0.85 |

HbAlc (hemoglobin Alc), HCT (hematocrit); Hb (hemoglobin); PLT (platelets); RBC (red blood cells); WBC (white blood cells); MCH
**p < 0.01 vs. control Example 5

A SALT OF LITHOSPERMIC ACID DECREASED THE ACTIVITY AND LEVELS OF HIGH GLUCOSE-INDUCED CELL SIGNALING MOLECULES AND EXTRACELLULAR MATRIX PRODUCTION AND SECRETION IN RENAL MESANGIAL CELLS

Hyperglycemia induced diabetic nephropathy has been studied experimentally by culturing renal cells (e.g., mesangial cells) in high glucose. Extracellular matrix molecules such as type IV collagen, laminin, and fibronectin protein synthesis are stimulated in rat and human mesangial cells cultured in high glucose (Ziyadeh F N, et al., J. Clin. Invest., 93:2431–2437 (1994); Kagami S, et al., Journal Clin. Invest., 93:2431–2437 (1994); Ayo S H, et al., Am. Journal Pathol., 136:1339–13348 (1930); Ayo S H, et al,. Amer. Journal Physiol., 260:F185–191 (1991); Danne T M, et al., Diabetes 42:170–177 (1993)). Mesangial cells cultured in the presence of high (30 mM) or normal (5.5 mM) glucose were used as a model system to discern the effects of a salt of lithospermic acid on the synthesis and secretion of extracellular matrix proteins and their cellular regulators.

Cell Cultures

Murine renal mesangial cells were used in these experiments. The mesangial cells (MES-13) were cloned from transgenic mice. The twenty-fifth passage of the originally plated cells was used in the experiments. MES-13 cells were grown in Dulbecco's Modified Eagle's Medium (DMEM) containing 15% fetal bovine serum (FBS), 1% streptomycin-penicillin mixture, fungizone 0.2 μg/mL, 44 mM $NaHCO_3$ and 14 mM HEPES at 37° C. in a humid atmosphere containing 5% $CO_2$ and 95% air. Subcultures were seeded from confluent stock cultures by trypsinization in Hanks balanced salt solution containing 0.5 mM EDTA and 0.025% trypsin and grown in DMEM containing 15% FBS for 24 hr to near confluence (80%). Near confluent cells were incubated with serum-free DMEM to arrest cell growth and synchronize cell cultures. After 24 hr, the media was changed to serum-free DMEM containing 5.5 mM (normal) or 30 mM (high) glucose and cells cultured for 5 days. Cells were then incubated with a salt of lithospermic acid at 25 μg/mL or 50 μg/mL for 24 hours.

A Salt of Lithospermic Acid Decreased High-Glucose Induced Protein Kinase C Activity The activation of protein kinase C (PKC) in diabetics transduces downstream signals and activates the MAPK cascade (Haneda M., et al., Diabetes 46:847–853 (1997)). The activation of MAPK, through MEK, can be responsible for excessive synthesis of extracellular matrix proteins in the glomeruli of diabetics (Haneda M., et al., Diabetes 46:847–853 (1997). MAPK is phosphorylate and activates Elk-1, one of the ternary complex factors (Janknecht R, et al., EMBO J.; 12:5097–5104 (1993)). Elk-1 activation subsequently increases the expression of c-fos and c-jun and excessive synthesis of extracellular matrix proteins in diabetic individuals (Studer R K, et al., Diabetes 42:118–126 (1993); Ayo S H, et al., Am. Journal Pathol. 136:1339–1348 (1930);. Ayo S H, et al., Amer. Journal Physiol. 260:f185–191 (1991); Haneda M, et al., Diabetologia 34:198–200 (1991); Fumo P. et al., Am. Journal Physiolo. 267:F632–F638 (1994)). Therefore, the ability of a salt of lithospermic acid to alter glucose-induced increases in PKC was evaluated using mesangial cell cultures.

The amount of PKC in lysates of cells cultured in presence of high glucose (30 mM) and normal glucose (control, 5.5 mM) was determined using a commercially available kit (Upstate Biotechnology, Lake Placid N.Y.). Briefly, 10 μl of the substrate cocktail, 10 μl of the inhibitor cocktail or assay dilution buffer II, 10 μl of the lipid activator (sonicated on ice for at least a minute before use), 10 μl of PKC (25–100 mg purified enzyme/assay), 10 μl of the cold adenosine 5-triphosphate and [$^{32}$P] ATP mixture were added to a sterile microcentrifuge tube and the final volume adjusted to 60 μl by the addition of assay dilution buffer II. Assay dilution buffers I and II were supplied by the manufacturer in the assay kit. The reaction mixture was incubated for 10 minutes at 30° C., spotted (25 μl) on to P81 paper squares, briefly washed with 0.75% phosphoric acid, followed by a wash with acetone. Assay squares were placed into vials and radioactivity determined by scintillation counting. PKC activity was expressed as pmol/min/protein. Significant differences between group means were determined using the unpaired or paired Student's t-test.

Figure 2:
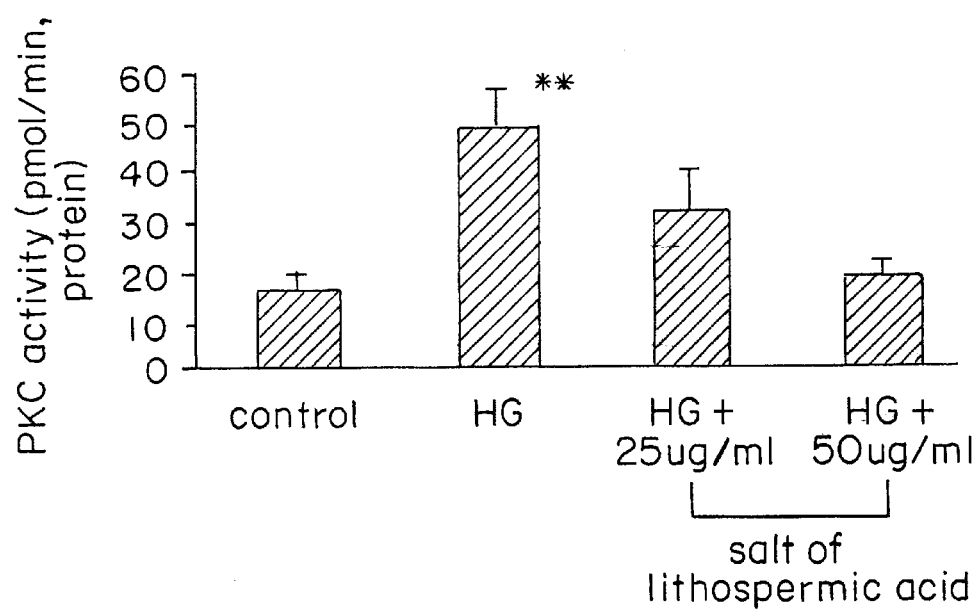
FIG. 2 depicts the effect of treatment with a salt of lithospermic acid (25 or 50 μg/mL) on high glucose (HG)-induced increases in protein kinase C (PKC) activity (pmol/min/protein) in mesangial cells.

As shown in FIG. 2, PKC activity was significantly ($p<0.01$) higher in cells cultured in the presence of high glucose (30 mM HG) for 5 days compared to cells cultured in normal glucose (control, 5.5 mM). The addition of a salt of lithospermic acid to cell cultures resulted in a significant ($p<0.01$) increase in PKC activity (FIG. 2). The effects of a salt of lithospermic acid on glucose-induced PKC activity were dose-dependent. The salt of lithospermic acid (50

μg/mL or 25 μg/mL) decreased PKC activity (FIG. 2). These data show that treatment of cells with a salt of lithospermic acid can decrease glucose-induced levels of PKC and, thus, can downregulate cell signaling pathways which have been implicated in diabetic nephropathy.

Preparation of Cell Lysates and Media for Western Blots

Western blotting was performed to assess relative changes in the levels of MEK1 and MEK2 protein (MEK-T); phosphorylated MEK1 and MEK2 (MEK-P); ERK1 and ERK2 (p42/p44 MAPK) protein (ERK-T); phosphorylated ERK1 and ERK2 (ERK-P); TGF-β1; and fibronectin in the mesangial cell lysates and conditioned media cultured in the presence (30 mM) and absence (5.5. mM) of high glucose.

Aliquots of mesangial cell lysates or culture media were added to SDS-gel electrophoresis sample buffer and heated at 95° C. for 15 min. Protein concentration in cell lysate and culture media samples was determined by the method of Lowry with BSA as a standard (Lowry, O. H., et al., J. Biol. Chem. 193:265–275 (1951)). Protein standards for MET-T, MEK-P, ERK-T, ERK-P, TGF-β1 and fibronectin were applied in parallel lanes with cell lysates and culture medium to 12.5 or 5% polyacrylamide gel and electrophoresed. Electrophoretically separated proteins were transferred to nitrocellulose membrane using standard protocols (Ausubel, et al., "Current Protocols in Molecular Biology," J. W. Wiley & Sons, New York, N.Y. (1998)).

Western blots were incubated with the primary antibodies to MET-T, MEK-P, ERK-T, ERK-P, TGF-β1, or fibronectin for 2 hr at room temperature (Ha, H., et al., J. Pharmacol. and Exp. Therap., 281:1457–1462 (1997)). The membranes were then washed in PBS-Tween-20 (0.3% v/v) for 1 hr, and incubated with peroxidase-conjugated secondary antibody for 2 hr at room temperature using routine protocols well known to the skilled artisan. (See Ausubel, et al., "Current Protocols in Molecular Biology," J. W. Wiley & Sons, New York, N.Y. (1998)). After washing, the antigen-antibody complexes were detected by enhanced chemiluminesence (Amersham International, England) and quantitated densitometry.

A Salt of Lithospermic Acid Decreased Glucose-Induced TGF-β1 Synthesis and Secretion TGF-β1 is expressed by cultured proximal tubules; and glomerular endothelial, pithelial and mesangial cells (Kaname S, et al., Kidney Int., 1319–1327 (1992); Haberstroh U, et al., Am. Journal Physiol., 264:F1966-F205 (1993); MacKay K, et al., Journal Clin. Invest., 83:1160–1167 (1989); Ziyadeh F N, et al,. Journal Am. Soc. Nephrol., 2:30 (1991)). TGF-β1 has been implicated in the pathogenesis of mesangial expansion in experimental glomerulonephritis (Border W A, et al., Nature, 360:361 (1990); Border W A, et al., Kidney Int., 41:566–570 (1992). Exposure to high glucose doubled the levels of mRNA encoding TGF-β1 in cultured mesangial cells (Wolf G, et al., Kidney Int., 42:647–656 (1992)). Increased expression of TGF-β1 is associated with the development of renal hypertrophy, an early feature of experimentally-induced and human diabetic nephropathy. Normalization of blood glucose levels with insulin treatment attenuates the increase in TGF-β1 expression (Border W A, et al., Diabetes Meab. Rev., 12:309–339 (1996); Shankland S J, et al., Kindey Int., 46:430–442 (1994)) and TGF-β1 induces hypertrophy in cultured cells (Border W A, et al., Diabetes Meab. Rev., 12:309–339 (1996)). Because these data indicate that TGF-β1 participates in renal hypertrophy and matrix expansion in the diabetic kidney, the effect of a salt of lithospermic acid on glucose induced increases in TGF-β synthesis and secretion was evaluated.

Figure 3:
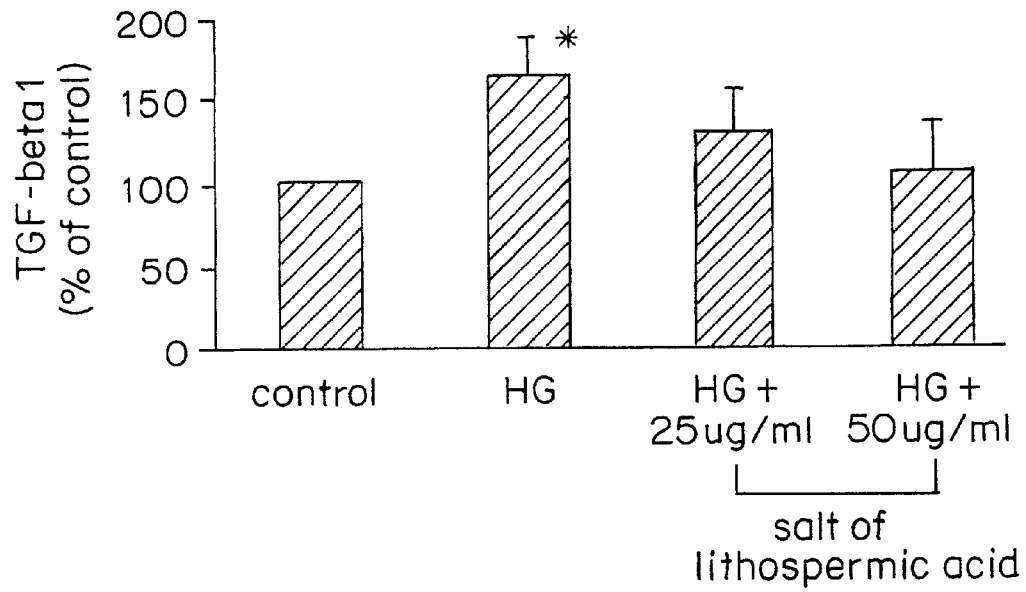
FIG. 3 depicts the effect of treatment with a salt of lithospermic acid (25 or 50 μg/mL) on high glucose (HG)-induced increases in TGF-beta1 secretion from mesangial cells.

TGF-β1 secretion was significantly increased in mesangial cultured in the presence of high glucose (30 mM) (FIG. 3). The addition of a salt of lithospermic acid (25 or 50 μg/mL) decreased TGF-β1 secretion from mesangial cells cultured in the presence of high-glucose (30 mM) (FIG. 3).

A Salt of Lithospermic Acid Decreased Glucose-Induced Fibronectin Synthesis and Secretion As shown in FIG. 3, the secretion of TGF-β1 mesangial cells was significantly increased in the presence of high glucose compared to cells cultured under normal glucose concentration. The salt of lithospermic acid decreased high glucose-induced TGF-β1 secretion. Since TGF-β1 stimulates fibronectin gene expression through a cAMP response element (Kreisberg J J, et al., Kidney Int. 46(4):1019–24 (1994)) and results in an accumulation of the extracellular matrix components in diabetic nephropathy (Border W A, et al., Diabetes Meab. Rev., 12:309–339 (1996)), the effects of salt of lithospermic acid on glucose-induced increases in fibronectin synthesis and secretion were evaluated.

Figure 4:
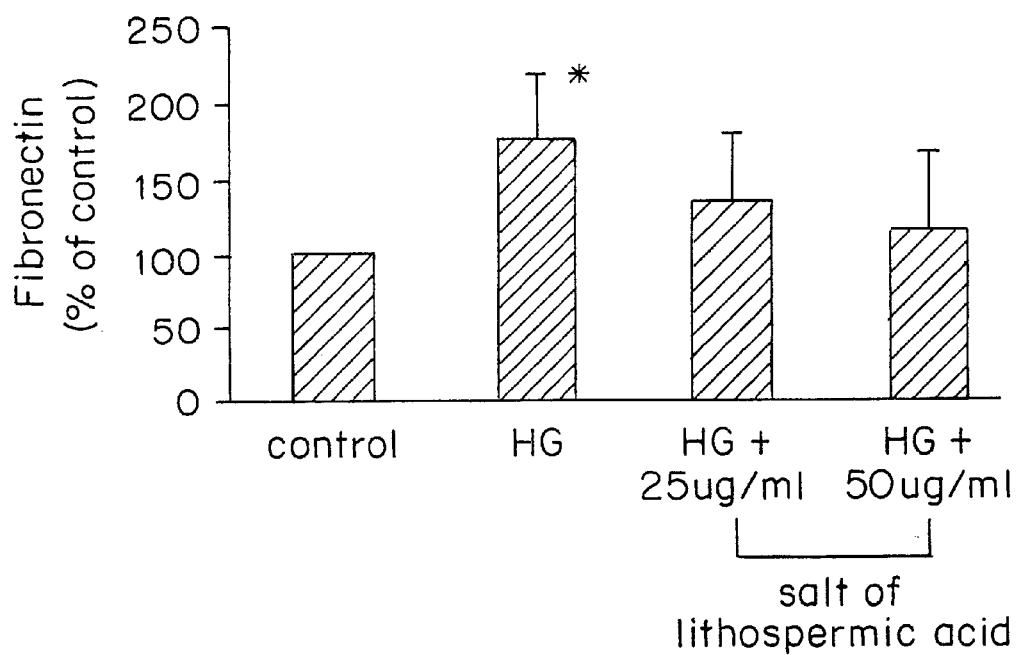
FIG. 4 depicts the effect of treatment with a salt of lithospermic acid (25 or 50 µg/mL) on high glucose (HG)-induced fibronectin secretion from mesangial cells.

Fibronectin secretion was increased when mesangial cells were cultured in the presence of high (30 mM) compared to normal or control (5.5 mM) glucose (FIG. 4). The high glucose-induced increase in fibronectin synthesis and secretion was decreased by the addition of a salt of lithospermic acid. The addition of a salt of lithospermic acid (50 μg/mL) decreased fibronectin levels to about that of control levels (FIG. 4).

A Salt of Lithospermic Acid Decreased Glucose-Induced Phosphorylation of MEK and ERK The MAPK cascade, including MEK and ERK, is an important signal transduction system. Activation of PKC in diabetes activates MAPK (Haneda M., et al., Diabetes 46:847–853 (1997)). Phosphorylation of the tyrosine and threonine residues of ERK is required for full activation and translocation of ERK to the nucleus. ERK-1 and ERK-2 are activated by phosphorylated MEK. The effects of a salt of lithospermic acid on the phosphorylation state of ERK2 and MEK2 were evaluated following exposure of mesangial cells to high glucose.

Figure 5:
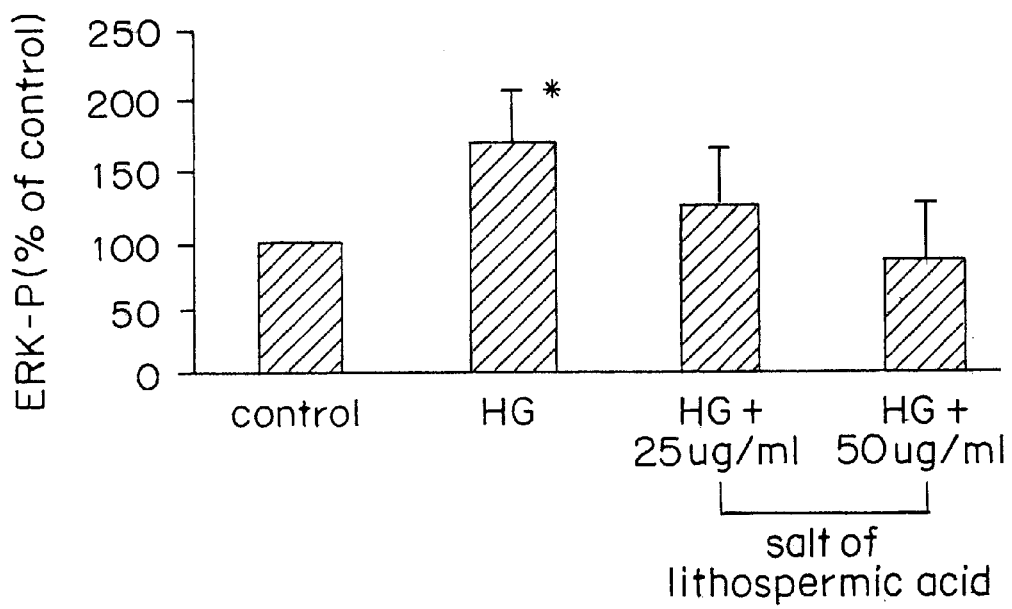
FIG. 5 depicts the effect of treatment with a salt of lithospermic acid (25 or 50 µg/mL) on high glucose (HG)-induced increases in phosphorylated extracellular-signal regulation kinase (ERK-P) in mesangial cells.
Figure 6:
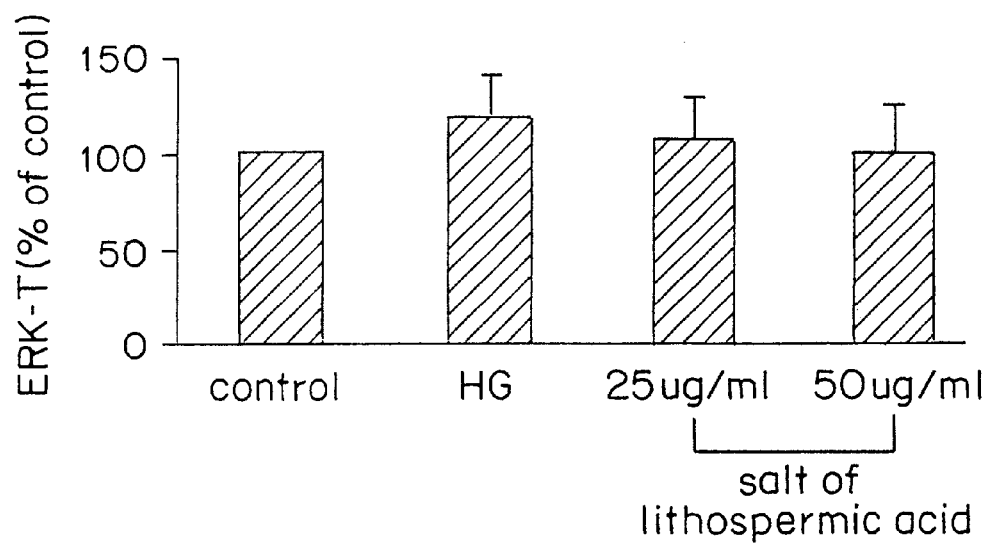
FIG. 6 depicts the effects of treatment with a salt of lithospermic acid (25 or 50 µg/mL) on the total ERK (ERK-T) synthesis in mesangial cells cultured in the presence of high-glucose.

The relative amount of phosphorylated ERK2 increased in mesangial cells cultured for 5 days in the presence of high glucose (30 mm) compared to normal glucose (5.5 mm) (FIG. 5), whereas the amount of total (ERK-T, phosphorylated and non-phosphorylated) ERK2 remained constant (FIG. 6). Treatment of cells cultured in the presence of high glucose, with a salt of lithospermic acid (50 μg/mL) resulted in a decrease in phosphorylated ERK2 to about control levels.

Figure 7:
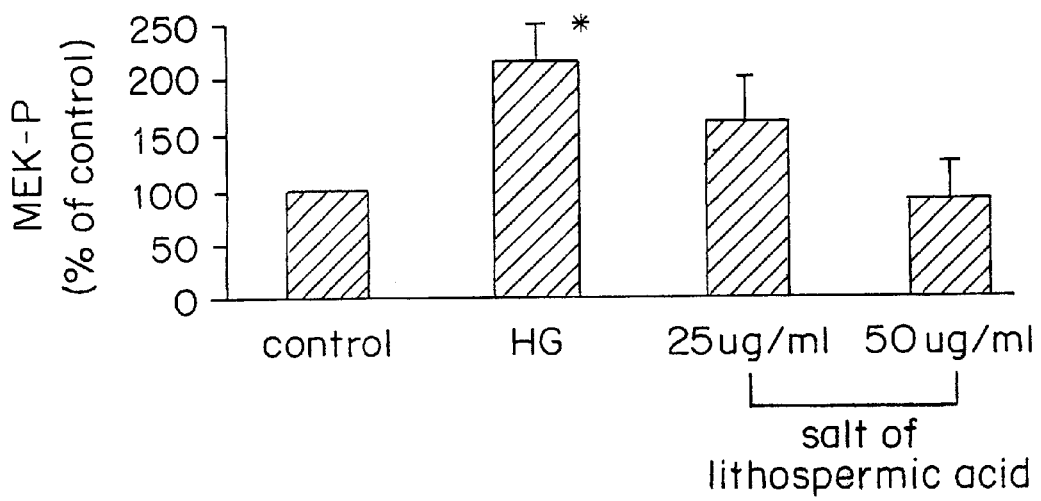
FIG. 7 depicts the effect of treatment with a salt of lithospermic acid on phosphorylated mitogen-activation protein kinase (MEK-P) synthesis in mesangial cells cultured in the presence of high-glucose.
Figure 8:
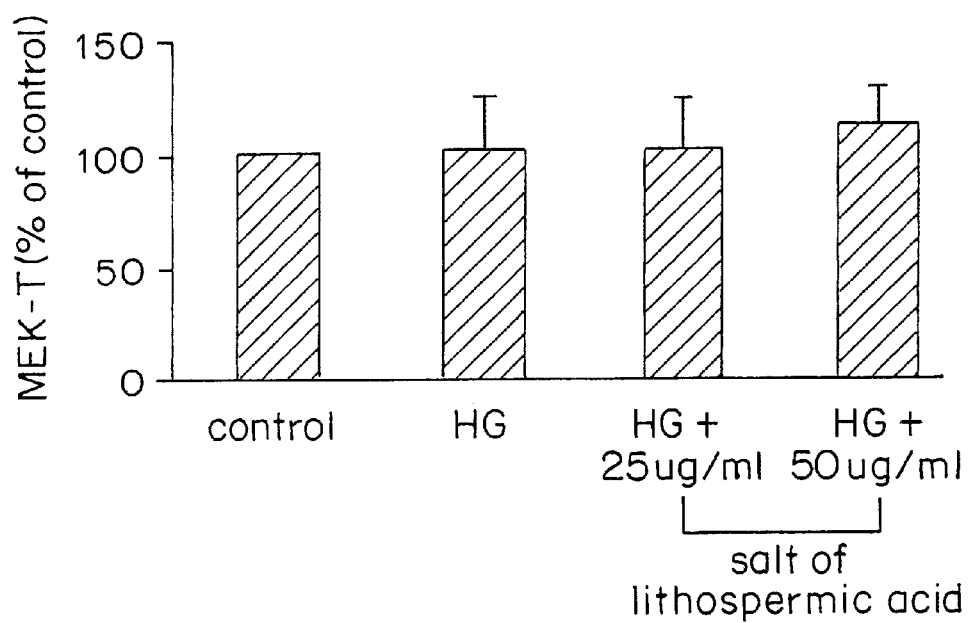
FIG. 8 depicts the effect of treatment with a salt of lithospermic acid (25 or 50 µg/mL) on high glucose (HG)-induced phosphorylated and nonphosphorylated MEK (MEK-T) in mesangial cells.

Similar to ERK, the amount of phosphorylated MEK2 (MEK P) was significantly increased in mesangial cells cultured under high glucose conditions compared to normal glucose (FIG. 7). As shown in FIG. 7, phosphorylated MEK2 approached control levels when cells cultured in the presence of high glucose were incubated with 50 μg/mL of salt of lithospermic acid. The total amount of MEK2 (MEK2-T, phosphorylated and nonphosphorylated) remained constant regardless of glucose concentration or treatment with a salt of lithospermic acid (FIG. 8).

These data show that under conditions of high glucose phosphorylation of ERK 2 and MEK2 is enhanced and treatment with a salt of lithospermic acid can restore the levels of phosphorylated ERK2 and MEK2 to about the levels observed in a control. An increase in the amount of phosphorylated ERK2 and MEK2 can be important in altering critical cell signaling pathways which can, for example, increase extracellular matrix production in renal cells and contribute to glomerular basement membrane accumulation resulting in diabetic nephropathy. Thus, a diminution in phosphorylated ERK2 and MEK2 in diabetic nephropathy, following treatment with a salt of lithospermic acid, can halt or decrease extracellular matrix deposition, thereby preventing the progression of the condition.

These data show that a salt of lithospermic acid can decrease the activity of PKC, MAPK cascades and TGF-$\beta$1 signaling pathways as well as decrease the synthesis and secretion of the extracellular matrix protein fibronectin. Inhibition of PKC activity by a salt of lithospermic acid can result in the inhibition of MAPK cascade and TGF-$\beta$1. Thus, a salt of lithospermic acid can reduce urinary protein in diabetic individuals potentially by altering PKC and MAPK mediated pathways.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating diabetic nephropathy in a diabetic individual comprising administering a Salviae Miltiorrhizae Radix herb, a Salviae Miltiorrhizae Radix mimic, or component thereof to the diabetic individual.

2. The method of claim 1, wherein the Salviae Miltiorrhizae Radix herb or the Salviae Miltiorrhizae Radix mimic is administered in a single dose.

3. The method of claim 1, wherein the Salviae Miltiorrhizae Radix herb or the Salviae Miltiorrhizae Radix mimic is administered in multiple doses.

4. The method of claim 1, further including the step of forming an extract of the Salviae Miltiorrhizae Radix or the Salviae Miltiorrhizae Radix mimic.

5. The method of claim 4, wherein the extract is formed by boiling the Salviae Miltiorrhizae Radix herb or the Salviae Miltiorrhizae Radix mimic.

6. The method of claim 1, wherein the diabetic individual is a noninsulin-dependent diabetic individual.

7. The method of claim 1, wherein the diabetic individual is an insulin-dependent diabetic individual.

8. A method of treating diabetic nephropathy in a diabetic individual, comprising the steps of:
   a) forming an extract of a Salviae Miltiorrhizae Radix herb or a Salviae Miltiorrhizae Radix; and
   b) administering the extract to the diabetic individual.

9. The method of claim 8, wherein the Salviae Miltiorrhizae Radix herb or the Salviae Miltiorrhizae Radix mimic is administered in a single dose.

10. The method of claim 8, wherein the Salviae Miltiorrhizae Radix herb or the Salviae Miltiorrhizae Radix mimic is administered in multiple doses.

11. The method of claim 8, wherein the diabetic individual is a noninsulin-dependent diabetic individual.

12. The method of claim 8 wherein the diabetic individual is an insulin-dependent diabetic individual.

13. A method of treating diabetic nephropathy in a diabetic individual, comprising the steps of:

a) determining the level of protein in urine of the diabetic individual;
   b) comparing the level of protein in urine with a control level; and
   c) administering a Salviae Miltiorrhizae Radix herb, a Salviae Miltiorrhizae Radix mimic, or component thereof to the diabetic individual to lower the level of protein in urine of the diabetic individual to about that of the control level.

14. The method of claim 13, further including the steps of forming an extract of the Salviae Miltiorrhizae Radix herb or the Salviae Miltiorrhizae Radix mimic.

15. The method of claim 14, wherein the extract is formed by boiling the Salviae Miltiorrhizae Radix herb or the Salviae Miltiorrhizae Radix mimic.

16. The method of claim 14, wherein the extract is administered in a single dose.

17. The method of claim 14, wherein the extract is administered in multiple doses.

18. The method of claim 13, wherein the level of protein in urine is determined at one or more points before, during and/or after administration of the Salviae Miltiorrhizae Radix herb or the Salviae Miltiorrhizae Radix mimic.

19. The method of claim 13, wherein the diabetic individual is a noninsulin-dependent diabetic individual.

20. The method of claim 13, wherein the diabetic individual is an insulin-dependent diabetic individual.

21. A method of treating diabetic nephropathy in a diabetic individual, comprising administering a salt of lithospermic acid to the diabetic individual.

22. The method according to claim 21, wherein the salt of lithospermic acid is salt of lithospermic acid.

23. The method of claim 21, wherein the salt of lithospermic acid is administered in a single dose.

24. The method of claim 21, wherein the salt of lithospermic acid is administered in multiple doses.

25. The method of claim 21, wherein the diabetic individual is a noninsulin-dependent diabetic individual.

26. The method of claim 21, wherein the diabetic individual is an insulin-dependent diabetic individual.

27. A method of treating diabetic nephropathy in a diabetic individual, comprising the steps of:

a) determining the level of protein in urine of the diabetic individual;
   b) comparing the level of protein in urine with a control level; and
   c) administering a salt of lithospermic acid to the diabetic individual to lower the level of protein in urine in the diabetic individual to about that of the control level.

28. The method of claim 27, wherein the salt of lithospermic acid is salt of lithospermic acid.

29. The method of claim 27, wherein administering the salt of lithospermic acid to the diabetic individual lowers the level of protein in urine in the diabetic individual to about that of the control level.

30. The method of claim 27, wherein the salt of lithospermic acid is administered in a single dose.

31. The method of claim 27, wherein the salt of lithospermic acid is administered in multiple doses.

32. The method of claim 27, wherein the diabetic individual is a noninsulin-dependent diabetic individual.

33. The method of claim 27, wherein the diabetic individual is an insulin-dependent diabetic individual.

34. The method of claim 27, wherein the level of protein in urine is determined at one or more points prior to, during and/or after the administration of the salt of lithospermic acid.

35. A method of treating diabetic nephropathy in a diabetic individual comprising administering to the diabetic individual salt of lithospermic acid or a salt of lithospermic acid mimic.

36. A method of treating diabetic nephropathy in a noninsulin-dependent diabetic individual comprising administering a Salviae Miltiorrhizae Radix herb, a Salviae Miltiorrhizae Radix mimic, or component thereof, to the noninsulin-dependent diabetic individual.

37. A method of treating diabetic nephropathy in a noninsulin-dependent diabetic individual, comprising the steps of:
   a) forming an extract of a Salviae Miltiorrhizae Radix herb or a Salviae Miltiorrhizae Radix mimic to form an extract; and
   b) administering the extract to the noninsulin-dependent diabetic individual.

38. A method of treating diabetic nephropathy in a noninsulin-dependent diabetic individual, comprising the steps of:
   a) determining the level of protein in urine of the noninsulin-dependent diabetic individual;
   b) comparing the level of protein in urine with a control level; and
   c) administering a Salviae Miltiorrhizae Radix herb, or a Salviae Miltiorrhizae Radix mimic, or component thereof to lower the level of protein in urine of the noninsulin-dependent diabetic individual to about that of the control level.

39. A method of treating diabetic nephropathy in a noninsulin-dependent diabetic individual comprising administering a salt of lithospermic acid to the noninsulin-dependent diabetic individual.

40. A method of treating diabetic nephropathy in a noninsulin-dependent diabetic individual, comprising the steps of:
   a) determining the level of protein in urine of the noninsulin-dependent diabetic individual;
   b) comparing the level of protein in urine with a control level; and
   c) administering a salt of lithospermic acid to the noninsulin-dependent diabetic individual to lower the level of protein in urine of the noninsulin-dependent diabetic individual to about that of the control level.

41. A method of treating diabetic nephropathy in a noninsulin-dependent diabetic individual comprising administering to the noninsulin-dependent diabetic individual salt of lithospermic acid or a salt of lithospermic acid mimic.

42. A method of treating diabetic nephropathy in an insulin-dependent diabetic individual comprising administering to the insulin-dependent diabetic individual salt of lithospermic acid or a salt of lithospermic acid mimic.

43. A method of treating microalbuminuria in an individual comprising administering a Salviae Miltiorrhizae Radix herb, a Salviae Miltiorrhizae Radix mimic, or component thereof to the individual.

44. A method of treating microalbuminuria in an individual, comprising the steps of:
   a) forming an extract of a Salviae Miltiorrhizae Radix herb or a Salviae Miltiorrhizae Radix mimic; and
   b) administering the extract to the individual.

45. The method of claim 44, wherein the extract is formed by boiling the Salviae Miltiorrhizae Radix herb or the Salviae Miltiorrhizae Radix mimic.

46. A method of treating microalbuminuria in an individual, comprising the steps of:
   a) determining the level of albumin in urine of the individual;
   b) comparing the level of albumin in urine with a control level; and
   c) administering a Salviae Miltiorrhizae Radix herb, a Salviae Miltiorrhizae Radix mimic, or component thereof to the individual to restore the level of albumin in urine in the individual to about that of the control level.

47. The method of claim 46, further including the step of forming an extract of the Salviae Miltiorrhizae Radix herb or the Salviae Miltiorrhizae Radix.

48. The method of claim 47, wherein the extract is formed by boiling the Salviae Miltiorrhizae Radix herb or the Salviae Miltiorrhizae Radix.

49. A method of treating microalbuminuria in an individual comprising administering a salt of lithospermic acid to the individual.

50. A method of treating microalbuminuria in an individual comprising administering salt of lithospermic acid to the individual.

51. A method of treating microalbuminuria in an individual, comprising the steps of:
   a) determining the level of albumin in urine of the individual;
   b) comparing the level of albumin in urine with a control level; and
   c) administering a salt of lithospermic acid to the individual to restore the level of albumin in urine in the individual to about that of the control level.

52. A method of treating microalbuminuria in an individual, comprising the steps of:
   a) determining the level of albumin in urine of the individual;
   b) comparing the level of albumin in urine with a control level; and
   c) administering salt of lithospermic acid to the individual to restore the level of albumin in urine in the individual to about that of the control level.

* * * * *